Figure 1:
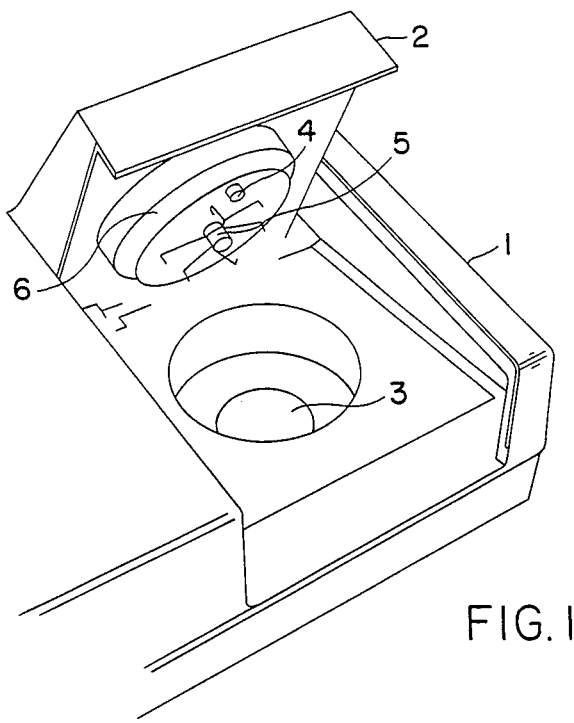

United States Patent [19]

Hagerlid et al.

[11] Patent Number: 4,844,782
[45] Date of Patent: Jul. 4, 1989

[54] METHOD IN STAINING AND DESTAINING OF ELECTROPHORETIC GELS

[75] Inventors: Peter K. Hagerlid, Uppsala, Sweden; Michael Hitchman, Glasgow, United Kingdom; Gunilla M. C. Jacobson, Uppsala, Sweden; Richard Wheeler, Warren, N.J.

[73] Assignee: Pharmacia AB, Uppsala, Sweden

[21] Appl. No.: 110,704

[22] PCT Filed: Feb. 12, 1987

[86] PCT No.: PCT/SE87/00066
§ 371 Date: Sep. 29, 1987
§ 102(e) Date: Sep. 29, 1987

[87] PCT Pub. No.: WO87/05111
PCT Pub. Date: Aug. 27, 1987

[30] Foreign Application Priority Data

Feb. 18, 1986 [SE] Sweden ................... 8600711

[51] Int. Cl.[4] .................................. C25D 1/12
[52] U.S. Cl. ....................... 204/180.1; 204/182.8; 204/182.9; 204/299 R
[58] Field of Search .......... 204/299 R, 182.8, 182.9, 204/180.1

[56] References Cited

U.S. PATENT DOCUMENTS 4,222,843  9/1986  Suzuki ................... 204/299 R
4,254,084  3/1981  Blum ..................... 422/81
4,612,106  9/1986  Kromer .................. 204/299 R

OTHER PUBLICATIONS

*Analytical Biochemistry*, vol. 112, No. 2, 1981, pp. 232-235, Terranova, A. C., "A Rotating Temperature-Controlled Water Bath for Isozyme Development in Polyacrylamide Slab Gels".
*Electrophoresis*, vol. 6, No. 8, 1985, pp. 408-09, Birgit C. et al., "Protein Staining of 6mm Diameter Sodium Dodecyl Sulfate-Polyacrylamide Gels Within One and a Half Hours".

*Primary Examiner*—John F. Niebling
*Assistant Examiner*—Isabelle Rodriguez
*Attorney, Agent, or Firm*—Fred Philpitt

[57] ABSTRACT

Method in the after-treatment of electrophoretic gels containing separated components, in that the gel is caused to rotate in a selected fixation, staining or destaining solution during at least a part of the total processing time which is calculated from given processing data with continuous temperature measurement.

7 Claims, 1 Drawing Sheet

U.S. Patent    Jul. 4, 1989    4,844,782

METHOD IN STAINING AND DESTAINING OF ELECTROPHORETIC GELS

The present invention relates to an improved method in the after-treatment of electrophoretic gels containing separated components, in that the gel is caused to rotate in a selected fixation, staining or destaining solution with continuous temperature measurement during at least a part of the total processing time calculated from given processing data.

Electrophoretic separation in a supportive phase in the form of a gel medium such as agarose or polyacrylamide, is usually performed by applying a sample to a very small area of the gel which contains an electrolytic liquid medium. Whereupon an electric field is applied over the gel. Then during a given period of time different components or different groups of components will migrate along distances of different lengths, depending on the experimental conditions such as the choice of buffer medium, pH and concomitantly of the charges on the sample components, or the choice of pore size in the gel matrix. When the electric field is removed and the separation is thus discontinued, the components of the sample will be found at different places along the migration path, often in the form of more of less distinct bands. Such a concentration of material to narrow bands is of paramount importance for subsequent analysis of the separation result; and special techniques have been developed for obtaining particularly sharp bands, for example isoelectric focusing.

Since the concentration of material in the bands is a high one as compared to their surroundings, diffusion from the bands into the surrounding gel regions will start as soon as the electric field is removed. Therefore, the first step performed after the separation will often be a treatment of the gel with a solution containing substances that will fix the bands to thereby prevent diffusion.

After the fixation step the position of the sample components have to be located on the gel for qualitative and/or quantitative analysis. In cases where the sample has originally contained e.g. fluorescent or radioactively labeled components detection can be carried out directly with the aid of a suitable detector; in most cases, however, the bands are subjected to staining for being rendered visible. This involves contacting the gel with a solution which contains dyes which will bind to the sample components, but not to the gel matrix. In this step it is an important requirement that staining be uniform, as otherwise a quantitative evaluation would be hampered by much uncertainty; consequently the supply of dye to the gel surface must be uniform, with ample time being allowed for the dye to bind to the components involved. The time actually required will depend on gel thickness, stirring rate, concentration of staining solution, and the temperature prevailing. According to the present state of the art staining is usually carried out by immersing the gel in a staining bath, and the bath is given a shake now and then. In order to ensure complete staining it is often preferred to leave the gel in the bath for a relatively long time, e.g. overnight.

During the staining step the dye will thus diffuse into the whole gel matrix, and for this reason it is necessary to wash off non-bound dye in a special so-called destaining bath. When the gel has been treated in this manner the bands will show up, and their positions, areas and colour intensities can be determined for a final evaluation.

Thus after the electrophoretic separation the gel is to be subjected to a plurality of treating steps: (1) fixation, (2) staining, and (3) washing for removal of non-bound dye, before evaluation is initiated. This sequence is customarily carried out by means of transferring the gel from container to container, the whole procedure taking usually at least six hours, the most common practice being actually to extend e.g. the staining step over one night. The containers may be provided with stirring means by which the solution is circulated in the container; but more often the container is simply subjected to shaking now and again, as mentioned above.

Procedures of this type may be accelerated by being carried out at an elevated temperature. In view of the fact that staining at e.g. 50° C. will be 2–3 times faster in typical cases than at 20° C., the time savings achievable in this manner may be quite considerable. Therefore, in order to obtain comparable results in repeated experiments it has been a requirement that the aforesaid processing parameters (gel thickness, concentrations, stirring rate, time and temperature) be maintained constant. This means that a strictly upheld thermostatic control has been required; and this applies also to storage vessels.

We have now found that much time can be saved and the process for preparing the gel for analysis after the separation step can be simplified considerably if suitable steps are carried out in one container common to all of them, and the process as a whole is controlled by means of a programmable electronic unit such as e.g. a microcomputer. The gel is placed into the container on a rotatable holder, for instance of the type shown in FIG. 2. The fixation, staining, destaining or wash solutions may be supplied to the container through one or more conduits which are also utilized for discharging. Control of the filling and discharging sequences of the container is performed by the electronic unit with the aid of pumps and valves, for example magnetic valves of a known type such as those employed in liquid chromatographic systems. The container is furthermore equipped with a temperature sensor from which temperature data are continuously fed to the control unit, and with heating means, e.g. an immersion heater, with the aid of which a predetermined temperature is obtained.

FIG. 1 is a schematic view of an equipment that may be used for carrying out the method of this invention. The apparatus part (1) has a circular cavity (3) which is to contain the particular solutions to be employed. Supply and withdrawal of solution is effected through one or more ducts in (3) which moreover contains a heating unit. The lid (2) has attached to it the temperature sensor (4) and the gel holder (5) which is rotatable. The motor producing this rotation is accommodated in portion (6) of lid (2).

Figure 2:
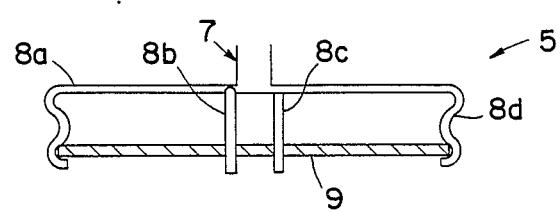

The gel holder (5) is also shown in FIG. 2, where (7) indicates the shaft by means of which the gel holder is mounted in the lid. The gel holder has four arms (8 a–d), the gel (9) being held in place in the manner as shown in the Figure.

When the gel has been positioned on the holder the lid is closed, whereupon the desired sequence of fixation, staining and destaining steps is initiated; and in this procedure and electronic unit controls the appertaining events comprising supply/withdrawal of solutions, temperature measurement, temperature control and rotation of the gel holder during at least a part of the processing time.

When calibration is carried out a step of the process, e.g. staining with Coomassie Blue, is performed with the concentrations and gel dimension that will be employed in subsequent experiments. The processing times, for several temperatures in a range corresponding to that which may be used later on, are measured in the system now maintained under strict thermostatic conditions. The results as referred to the value at 20° C. normalized to 1.0 may typically be the following: 0.5 at 5° C.; 1.4 at 30° C.; 1.8 at 40° C.; 2.3 at 50° C. The value 0.5 at 5° C. thus means that the reaction rate at this temperature is half the 20° C. reaction rate. When the electronic unit has been fed with these measurement data, from which all the other values within the aforesaid temperature range can readily be extrapolated, the process may then be carried out at any desired temperature within that range. The temperature in the container is recorded continuously, as well as the processing time. If the processing time for 20° C. has been determined to be 12 minutes when the gel is rotated continuously at a frequency of 2 Hz then of course this step is stopped after this 12 min. period in the case of the temperature being constant. If, however, the solution has had a temperature of 5° C. (typical refrigerator temperature) in the stage when it was pumped into the container, then a longer processing time is calculated from the aforesaid calibration curve which compensates for the initially lower than 20° C. temperature. This is effected by adding up the process contributions during each unit of time.

It is easy to see the advantages in this method. Thus, it is possible to select a high temperature such as e.g. 50° C. as the final processing temperature but to nevertheless have entirely different temperatures in the solutions while they are being fed to the container by pumping; this is feasible because the prolongation of the total processing time thus necessitated can be calculated correctly from the calibration curve. It is only the container itself that has to be subjected to thermostatic control in this case; this opens the possibility of handling the solutions more quickly and of using simpler equipment.

In the method of this invention, the rotation of the gel in a holder replaces stirring of the solution by means of e.g. a magnetic stirrer. This has been found to give a considerably improved result. A suitable rotation rate has been found by us to be within the range of from 0.1 to 4 Hz, preferably 0.3 to 0.5 Hz if a holder of the FIG. 1 design is employed. Rotation need not be continuous but should proceed during at least 20%, preferably at least 50% of the processing time. Alternative embodiments within the scope of the inventive concept comprise for instance alternative gel holders and drive means of a type that will permit reversal of the direction of rotation.

We claim:

1. A method for the after-treatment of electrophoretic gels that contain separated components which comprises
   (a) establishing an after-treatment zone that includes
      (1) at least one inlet and at least one outlet for the introduction and removal of after-treatment fluids to and from said zone,
      (2) a lid-mounted holder for rotary movement within said zone, and
      (3) a temperature sensor and heating means for maintaining a predetermined temperature within said zone,
   (b) placing an electrophoretic gel in said gel holder,
   (c) introducing at least one after-treatment composition into said after-treatment zone, and
   (d) rotating said electrophoretic gel within said after treatment zone while the gel is being contacted with said after-treatment composition.

2. A method according to claim 1 wherein said gel is rotated during at least 20% of the total time of after-treatment.

3. A method according to claim 1 wherein said gel is rotated during at least 50% of the total time of after-treatment.

4. A method according to claim 1 wherein said after-treatment includes the steps of fixation, staining and destaining.

5. A method according to claim 2 wherein said after-treatment includes the steps of fixation, staining and destaining.

6. A method according to claim 3 wherein said after-treatment includes the steps of fixation, staining and destaining.

7. A method for the after-treatment of electrophoretic gels that contain separated components which comprises
   (a) establishing an after-treatment zone that includes
      (1) at least one inlet and at least one outlet for the introduction and removal of after-treatment fluids to and from said zone,
      (2) a lid-mounted gel holder mounted for rotary movement within said zone, and
      (3) a temperature sensor and heating means for maintaining a predetermined temperature within said zone.
   (b) placing an electrophoretic gel in said lid-mounted gel holder,
   (c) introducing at least one after-treatment composition into said after-treatment zone,
   (d) rotating said electrophoretic gel within said after-treatment zone relative to said after-treatment solution so that the gel is rotated with respect to said after-treatment composition, and
   (e) continuously measuring and adjusting the temperature and adjusting the processing time to compensate for variations in temperature when a new after-treatment composition is fed into said after-treatment zone.

* * * * *